(12) United States Patent
Gjerde

(10) Patent No.: US 10,307,693 B2
(45) Date of Patent: Jun. 4, 2019

(54) METHODS FOR PURIFYING BIOLOGICAL CELLS

(71) Applicant: Douglas T. Gjerde, Saratoga, CA (US)

(72) Inventor: Douglas T. Gjerde, Saratoga, CA (US)

(73) Assignee: Douglas T. Gjerde, Saratoga, CA (US)

( * ) Notice: Subject to any disclaimer, the term of this patent is extended or adjusted under 35 U.S.C. 154(b) by 0 days.

(21) Appl. No.: 15/167,752

(22) Filed: May 27, 2016

(65) Prior Publication Data

US 2016/0375377 A1   Dec. 29, 2016

Related U.S. Application Data

(63) Continuation of application No. 14/181,656, filed on Feb. 15, 2014, now Pat. No. 9,370,732.

(60) Provisional application No. 61/765,541, filed on Feb. 15, 2013.

(51) Int. Cl.
| | |
|---|---|
| *B01D 15/22* | (2006.01) |
| *B01D 15/42* | (2006.01) |
| *G01N 1/40* | (2006.01) |
| *B01L 3/02* | (2006.01) |
| *B01D 15/38* | (2006.01) |
| *B01D 15/14* | (2006.01) |
| *G01N 1/34* | (2006.01) |
| *G01N 15/00* | (2006.01) |
| *G01N 15/10* | (2006.01) |
| *G01N 35/04* | (2006.01) |
| *G01N 15/14* | (2006.01) |
| *G01N 35/10* | (2006.01) |

(52) U.S. Cl.
CPC ............ *B01D 15/22* (2013.01); *B01D 15/14* (2013.01); *B01D 15/3809* (2013.01); *B01D 15/424* (2013.01); *B01L 3/0275* (2013.01); *G01N 1/34* (2013.01); *G01N 1/405* (2013.01); *B01L 2200/0647* (2013.01); *B01L 2300/069* (2013.01); *G01N 15/1463* (2013.01); *G01N 2015/008* (2013.01); *G01N 2015/1006* (2013.01); *G01N 2035/0434* (2013.01); *G01N 2035/1053* (2013.01)

(58) Field of Classification Search
None
See application file for complete search history.

(56) References Cited

U.S. PATENT DOCUMENTS 7,482,169 B2 *   1/2009   Gjerde ................... B01J 20/285
                                                                210/198.2

OTHER PUBLICATIONS

Kumar, Ashok; Bhardwaj, Aditi; "Methods in cell separation for biomedical application: cryogels as a new tool" Biomedical Materials, 3, 2008 (Year: 2008).*

(Continued)

*Primary Examiner* — David W Berke-Schlessel
(74) *Attorney, Agent, or Firm* — Sue S. Kalman

(57) ABSTRACT

This invention relates to devices and methods for purifying biological cells. For example, viable tumor, stem, immune and sperm cells can be purified from a complex biological sample using a pipette tip column. Methods of the invention can aid research, diagnosis and treatment of cancer.

9 Claims, 3 Drawing Sheets

(56) References Cited

OTHER PUBLICATIONS

Huang, TS; et al; "Immobilization of antibodies and bacterial binding on nanodiamond and carbon nanotubes for biosensor applications" Diamond and Related Materials, 13, 1098-1102, 2004 (Year: 2004).*

McDonagh, Charlotte; et al; "Engineered antibody—drug conjugates with defined sites and stoichiometries of drug attachment" Protein Engineering, Design & Selection, 19, 299-307, 2006 (Year: 2006).*

\* cited by examiner

METHODS FOR PURIFYING BIOLOGICAL CELLS

CROSS-REFERENCE TO RELATED APPLICATIONS

This patent application is a continuation of U.S. patent application Ser. No. 14/181,656, filed Feb. 15, 2014, which claims the benefit of U.S. Provisional Application No. 61/765,541, filed Feb. 15, 2013, which is incorporated by reference herein.

FIELD OF THE INVENTION

This invention relates to devices and methods for purifying biological cells. For example, viable tumor, stem, immune and sperm cells can be purified from a complex biological sample using columns, such as pipette tip columns.

SUMMARY OF THE INVENTION

In the present invention, cells are purified from a biological sample using a column. The sample is passed through the column and cells are captured on the medium within the column. Following capture, the column is washed to remove material that is not specifically bound to the column medium. Cells are recovered by passing an eluent through the column.

BACKGROUND OF THE INVENTION

The primary technology for capturing cells is magnetic beads. In this technology, a suspension of beads is used to treat a sample containing cells. The magnetic beads contain a tag or chemical entity that is selective for cells or for a certain cell type within the sample. After the cells become associated with the magnetic beads, a magnet is used to collect the magnetic beads and captured cells. The magnetic beads may be re-suspended several times with wash solutions to clean the cells. Finally, a solution may be used to release the cells from the beads. A magnetic is used to separate the magnetic beads from the cells.

The magnetic-activated cell sorting (MACS) method available from Miltenyl Biotec allows cells to be separated by incubating with magnetic nanoparticles coated with antibodies against a particular surface antigen. Cells expressing this surface antigen attach to the magnetic nanoparticles. Afterwards the cell solution is transferred on a column placed in a strong magnetic field. In this step, the cells attached to the nanoparticles (expressing the antigen) stay on the column, while other cells (not expressing the antigen) flow through.

With the MACS method, the cells can be separated either positively or negatively with respect to particular antigens. With positive selection, cells expressing the antigen(s) of interest, which attached to the magnetic column, are washed out to a separate vessel, after removing the column from the magnetic field. This method is useful for isolation of a particular cell type, for instance CD4 lymphocytes. In negative selection, the antibody used is directed against surface antigen(s) known to be present on cells that are not of interest. After administration of the cells/magnetic nanoparticles solution onto the column the cells expressing these antigens bind to the column and fraction that goes through is collected, as it contains almost no cells with undesired antigens.

Rare circulating tumor cells (CTCs) present in the bloodstream of patients with cancer provide a potentially accessible source for detection, characterization, and monitoring of nonhematological cancers. A microfluidic device, the Harvard CTC-Chip, has been used to capturing these epithelial cell adhesion molecule (EpCAM)-expressing cells using antibody-coated microposts. In a first generation device called 78,000 antibody-functionalized microposts were used to separate cells. Another microfluidic mixing device called the herringbone-chip is made up of parallel slanted channels (Li et al, Lab Chip, 13, 602).

In one technology, cells are collected on a flow through column at very slow flow rate and very low volumes making them difficult to use. The chip column does not contain a frit because the frit would prevent passage of the cells or trap, damage or kills the cells. But instead of a column frit a thin passage channel was used at the base of the chip to let the liquid flow through the column (Kralj et al. Lab Chip, 2012, 12, 4972-4975).

The EpCAM-based technique is very low throughput. A suspension of whole blood was pumped from 3 mL syringes at 0.2 mL/h for 1 h through the microfluidic packed bed to allow immobilization of the cancer cells. At this rate 5 hours is need to process 1 mL of blood. This may be an improvement over the Harvard CTC-chip, but still does not solve some fundamental issues with EpCAM based capture. The throughput is impractical and it too slow. Multiple channels can be used, but that will dramatically increase the imaging and staining area, making it difficult to perform high resolution cytomorphological analysis These magnetic bead methods and micro or chip based columns are slow and do not produce pure cell populations. There exists a need for a column technology that captures cells at high concentrations and then recovers the cells at high purity.

BRIEF DESCRIPTION OF THE INVENTION

In this work, we describe an invention for the separation and purification of cells, including viable cells and cancer cells. A biological sample containing cells is passed through a column. In some embodiments, the column is a pipette tip column. In some embodiments, the flow of sample through the column is bidirectional. In some embodiments the flow rate is quite high so that the cell purification can be performed in less than 1 hour. In certain embodiments, cells can be purified from a sample in less than 30 minutes.

BRIEF DESCRIPTION OF THE DRAWINGS

FIG. 1A depicts an aspiration step. FIG. 1B depicts an expulsion step.

FIG. 3A depicts and aspiration step and FIG. 3B depicts and expulsion.

DETAILED DESCRIPTION OF THE INVENTION

Figures 1A, 1B:
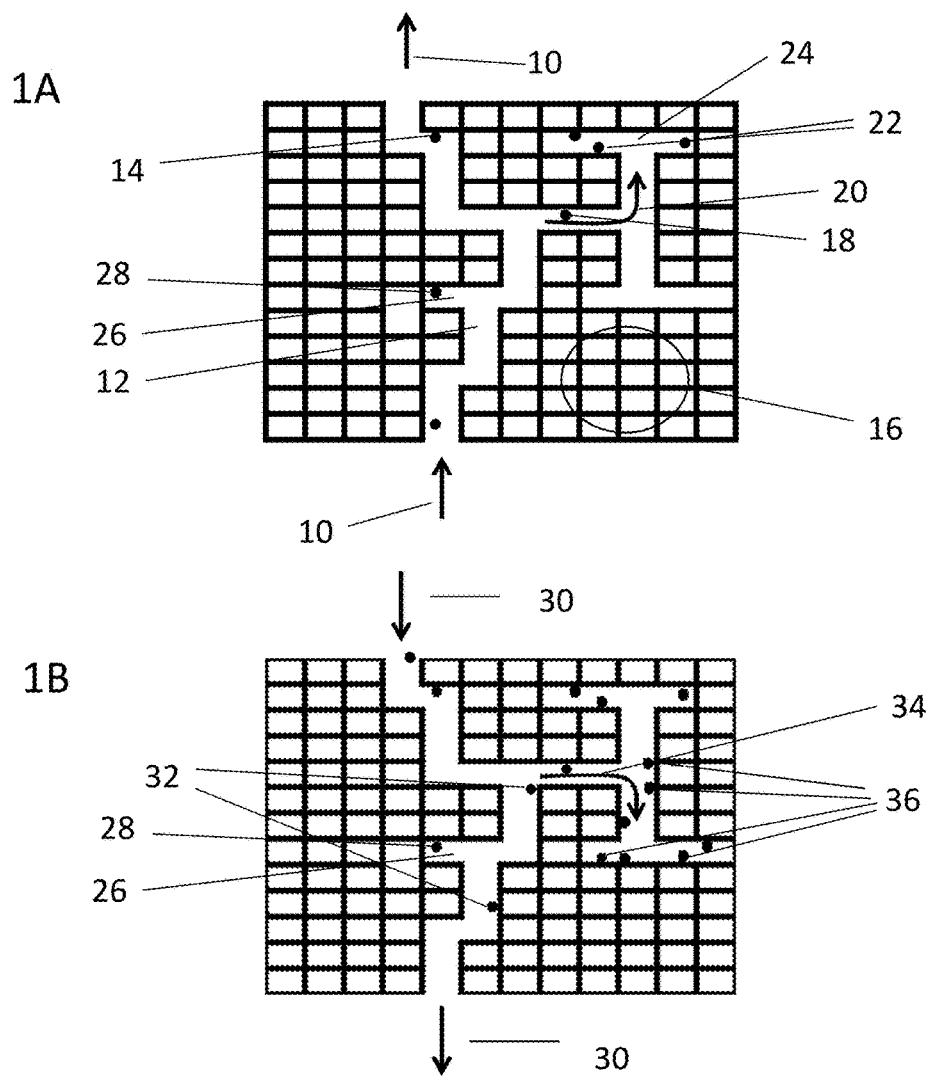
FIGS. 1A-B. Stylistic depiction of flow path, nooks and traps in a column.

It is quite remarkable that intact cells and even viable cells can be purified using the columns and methods of the invention. Cells are defined herein as membrane-bound structures that occur as functional independent units of life (such as in unicellular organisms, e.g. bacteria, protozoa, etc.), or as structural or fundamental units in a biological tissue specialized to perform a particular function in multicellular organisms (e.g. plants and animals).

Cells are quite fragile and can rupture easily from a variety of physical conditions such as encountering an object, shearing force, turbulence or incorrect solute concentration. Mechanical cell lysis can be induced by a collision of the cells with micro beads. In fact, this is a common method for lysing cells. However, even a little damage, even one breach of the cell membrane is enough to cause catastrophic damage to a cell. Viable cells can die simply from incorrect storage, processing, transport, exposure to incorrect temperature (heat or cold), pH, medium, vessel, etc.

It is surprising that cells can remain intact even after subjecting them to the methods of the invention. Specifically, cells purified via the instant invention are subjected to a repeated back and forth flow, battering motion through a fritted column containing a bed of medium. Cells are flowed through a fritted column containing a bed of medium. Most commercially-available methods for cell isolation involve the use of magnetic beads. To the inventors' knowledge, cells have never been isolated from fritted columns using the flow rates disclosed herein or using back and forth flow.

As described above, the columns of the invention contain a bed of medium onto which the cells are captured. The bed can be comprised of beads or particles held in the column by at least one frit. In certain embodiments, the bed is retained in the column with two frits; one below the bed and one above the bed. It is quite surprising that cells can pass through the frit(s) and the bed of medium and maintain their integrity and in some cases, their viability.

Consider the physical environment of a liquid sample comprised of cells passing through the frit and bed of medium within a column. The channels through which a cell might flow are not open or linear. Instead, the flow path would consist of a variety of interwoven channels, each with varying and perhaps restrictive diameters, and many possible dead ends marked by repeated turns, bends, winding and twisting. This tortuous path environment is advantageous for the capture of small molecule analytes because the fluid (containing the analyte) gets extensive exposure to the column matrix. However, a cell travelling or flowing through this environment could easily be trapped. Of course, physically trapping cells within the column matrix is an undesirable outcome quite distinct from targeted cell capture strategies such as affinity binding. Cells that become physically trapped cannot be recovered with an eluent or desorption solvent. Furthermore, if cells are trapped even temporarily, they could readily rupture or die.

FIGS. 1A and 1B illustrate the surprising nature of the invention. It is a stylistic depiction of the many potential hazards and pitfalls that could be encountered by cells travelling through a column using bidirectional flow. FIG. 1A depicts an aspiration step in which the flow direction 10 is upward. The matrix of the material (e.g., a polymer) is depicted by closed squares 16. Cells cannot penetrate matrix 16. The flow path through a column bed contains many potential nooks and traps for cells. A clear unrestricted flow path 12 enters and exits the bed. Some cells (e.g., 14) may be captured by the column in flow path 12. As the flow proceeds, many or most of the cells 18 enter dead end flow paths 20 to trap the cells 22 in dead end or restricted passages 24. There are also nooks (e.g., 26) just off flow path 12 that may trap cell 28.

FIG. 1B depicts the fate of cells resulting from back and forth flow through the column. The flow direction 30 is in a downward direction, reversed from upward direction 10 shown in FIG. 1A. Although increased residence time may allow a greater number of cells 32 to be captured, this reversal of the flow direction 34 can also exacerbate the undesired trapping of many cells 36. It should be noted that cell 28 remains trapped in nook 26.

Figure 2:
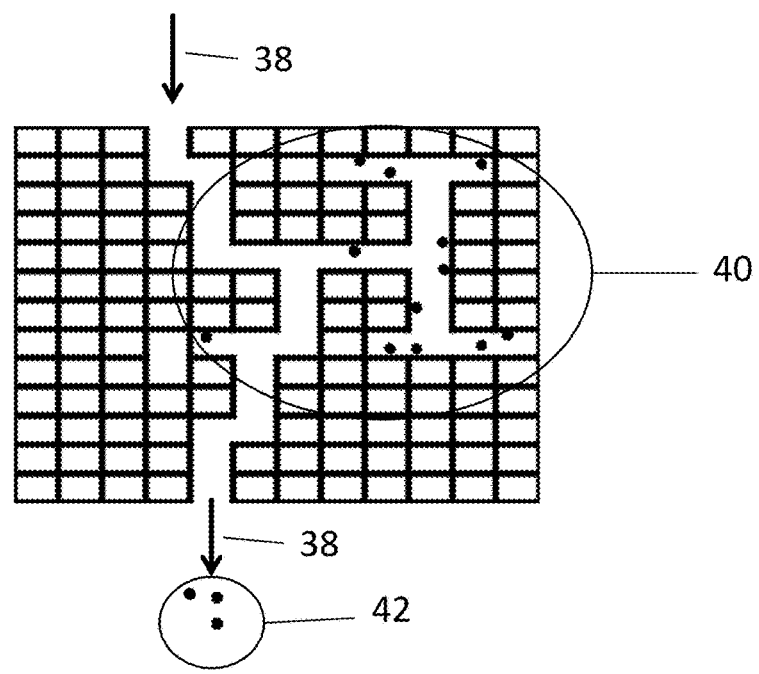
FIG. 2. Elution of cells from a column shown in FIG. 1B.

FIG. 2 depicts the elution of cells from a column. The recovery of cells from a column is attempted with a downward flow direction 38. Most of the cells 40 remain irreversibly trapped. A few cells 42 may be recovered but may or may not be intact. In addition to the risk of cell trapping, a person of skill in the art would expect the column environment or materials to be inhospitable to cells. It is desirable to recover intact and even viable cells. Intact cells are defined herein as cells having no holes or ruptures in their membrane. The column materials or surfaces, such as the frit or column walls might be incompatible with the cell integrity or viability. Protrusions present in the column wall, bed or frit could easily damage or rupture cells.

Figure 3:
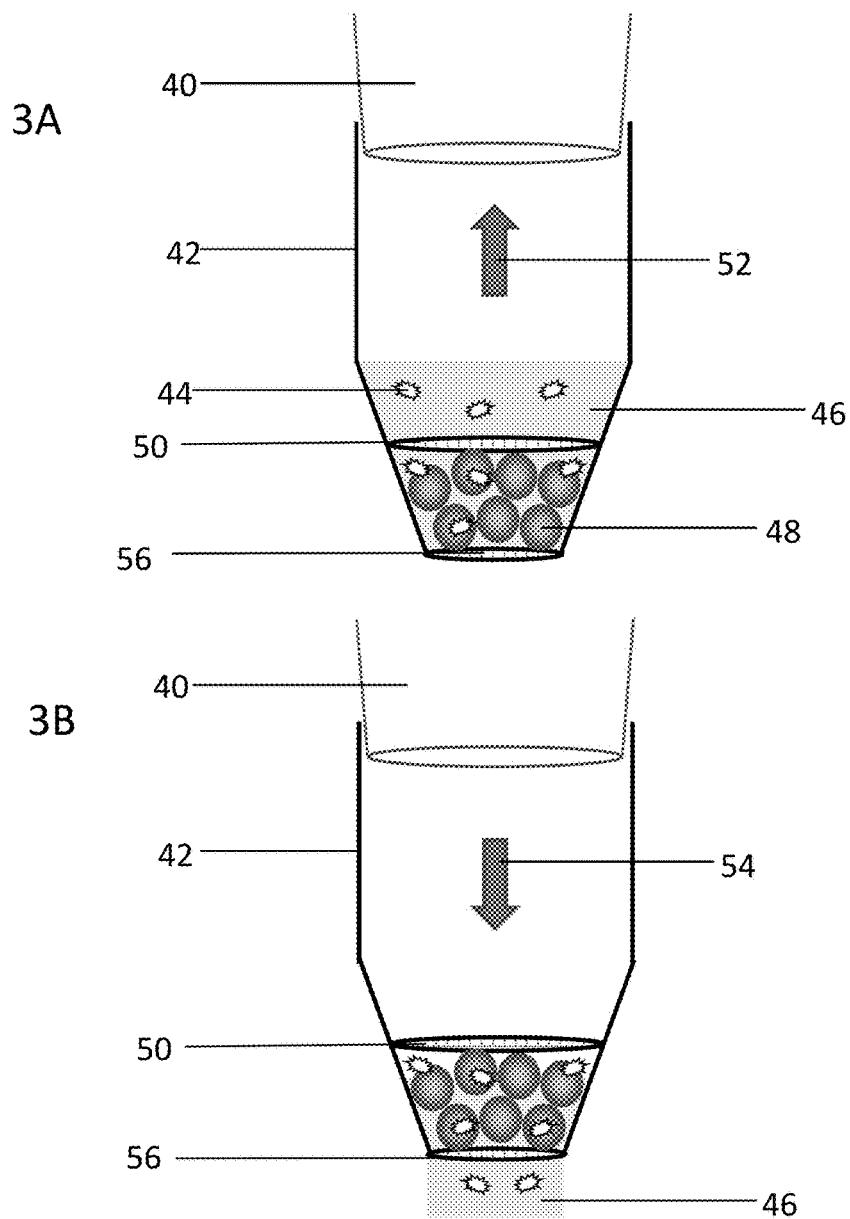
FIGS. 3A-B. Depiction of the column and method of the invention.

FIGS. 3A and 3B depict a column and method of the invention. Cells in a liquid sample are passed through the column using back and forth flow. In these embodiments, the upper end of the column is operatively engaged with pump 40 and sample 46 containing cells 44 is aspirated and expelled through the lower end of the column. During the aspiration step, the sample travels in direction 52, upwards in through lower frit 56 into the bed of beads 48 and then continues through upper frit 50 (FIG. 3A). During expulsion, the sample 46 travels back downward in direction 54, back through upper frit 50, into the bed of medium, through lower frit 56 and exits the bottom of the column (FIG. 3B). These aspirations and expulsions can be repeated multiple times, the desired result being that intact cells are captured by the medium.

Although column flow is harmful to cells, intuitively, it seems that the flow paths resulting from back and forth flow would be even more perilous for cells than unidirectional flow, especially when the goal is recovery of intact cells or viable cells. Cells would pass through the frit(s) multiple times from both directions, increasing the probability of cell damage or death.

Even when slow rates are used, cells can travel through the column at relatively high linear velocities. A high linear velocity would be expected to exacerbate the potential problems listed above. For example, a cell could become lodged in a dead end with greater force, making it more difficult to free the cell. While a cell travelling at a relatively slow velocity might slide or sidle around an obstacle, a cell travelling at a high velocity might be ruptured.

The starting sample contains viable cells and can be from any biological source. For example, cells can be captured from biological fluids such as blood or semen or tissues such as brain or tumor tissue. The invention is not limited to particular tissue type or cell type; cells captured by the methods of the invention can be eukaryotic or prokaryotic cells. In certain embodiments, the method can be used for the analysis of cells from crime scene samples.

In some embodiments, the columns used for the methods of the invention are pipette tip columns. Pipette tip columns are defined herein as columns capable of operative engagement with a pipette or liquid handing robot. In some embodiments, the columns can be integrated into a multiwell plate. In other embodiments, the columns are adapted to engage a syringe or syringe pump.

The method can be performed in an automated or semi-automated fashion. The term "semi-automated" is defined as a process by which two or more samples, columns or tubes are processed simultaneously or by which the sample process is at least partially performed by a timed computer or processor controlled program. The term "automated" is defined as a process by which sample processing is performed by a robotic system controlled by a timed computer program.

The columns of the invention are comprised of a medium on which the cells are captured. The medium can be beads or particles. In certain embodiments, the column medium can be a monolith, a filter or a combination of materials. In some embodiments, the bead size is quite large, on the order of 100-900 microns or in some cases even up to a diameter of 3 mm. In other embodiments, the bead size is that used in conventional columns, on the order of 45-150 microns. The average particle diameters of beads of the invention can be in the range of about 20 µm to several millimeters, e.g., diameters in ranges having lower limits of 20 µm, 30 µm, 40 µm, 50 µm, 60 µm, 70 µm, 80 µm, 90 µm, 100 µm, 150 µm, 200 µm, 300 µm, or 500 µm, and upper limits of 20 µm, 30 µm, 40 µm, 50 µm, 60 µm, 70 µm, 80 µm, 90 µm, 100 µm, 150 µm, 200 µm, 300 µm, 500 µm, 750 µm, 1 mm, 2 mm, or 3 mm.

Various mechanisms can be used for cell capture on the medium. Non-limiting examples include a functional group that has affinity for the cells, use of a tagged antibody, ion exchange, a tagged aptamer and an antibody loaded resin (Pro A, G etc.), covalently bonded linkers (alkyl thio, etc.) and hydrogen bonded linkers.

The medium may be held in the column with at least one frit positioned below the bed of medium. This lower frit may lie at the lower end of the column or it may be positioned some distance above the lower end. In certain embodiments, a second frit is positioned above the bed. The bed can be packed between two frits using a light force packing method. The goal of light force packing is not to compact the bed or introduce restrictive flow channels. In alternative embodiments, the column lacks a top frit. In still other embodiments, there is a gap between the bed of medium and the top frit. This gap is referred to as an air gap.

The column frits should have a pore size small enough to contain the medium but large enough for cells to pass through. Frits of the invention preferably have pore openings or mesh openings of a size in the range of about 5-500 µm. In preferred embodiments, the frits can be quite thin to lessen the probability that cells will become trapped within the frit. It is important that the frit does not provide dead-end or restricted-end flow paths that could potentially trap or damage cells. In some embodiments, a screen or fabric frit is utilized.

In some embodiments, the sample is aspirated and expelled through the lower end of the column. This method is referred to as back and forth or bidirectional flow. In these embodiments, a pump, such as a liquid handling robot is operatively engaged with the upper end of the column and the sample is aspirated and expelled through the lower end of the column. In other embodiments, unidirectional flow is used. In these embodiments, the sample is added to the upper end of the column and flows in a downward direction through the column and out the lower end. The sample can be passed through the column with the use of a pump, a vacuum or even gravity.

A relatively high solvent flow rate having high linear velocity can be used with the methods of the invention. Columns of the invention can accommodate a variety of flow rates, and the invention provides methods employing a wide range of flow rates, oftentimes varying at different steps of the method. In various embodiments, the flow rate of liquid passing through the media bed falls within a range having a lower limit of 0.01 mL/min, 0.05 mL/min, 0.1 mL/min, 0.5 mL/min, 1 mL/min, 2 mL/min, or 4 mL/min and upper limit of 0.1 mL/min, 0.5 mL/min, 1 mL/min, 2 mL/min, 4 mL/min, 6 mL/min, 10 mL/min or greater. For example, some embodiments of the invention involve passing a liquid though a packed bed of media having a volume of less than 100 µL at a flow rate of between about 0.1 and about 4 mL/min, or between about 0.5 and 2 mL/min, e.g., a small packed bed of extraction media as described elsewhere herein. In another example, other embodiments of the invention involve passing a liquid though a packed bed of media having a volume of less than 25 µL at a flow rate of between about 0.1 and about 4 mL/min, or between about 0.5 and 2 mL/min. Column with larger bed volumes e.g. 200 µL to 10 mL and 1 mL to 50 mL may use even faster flow rates.

Columns used in the invention contain material capable of capturing cells. Cells are large and bulky. As cells flow through the column, their orientation may not be ideal making it difficult to capture them with affinity groups. In certain embodiments, the columns are comprised of a packed bed of medium. In other embodiments, the columns can contain a bed that is not tightly packed or fluidized. The medium can be comprised of beads or particles. When a sample containing viable cells is passed through the column, the cells are captured by the material within the column. In some embodiments, the column is operated in a cold room while in other embodiments, the column can be operated at room temperature or at a temperature greater than room temperature.

After the capture step, the columns are washed with buffer or water to remove any material that is not specifically bound to the column medium. The wash liquid can be passed through the column by any means or rate described above for the sample. The wash step may be repeated once to several times.

Following the column wash, the cells can be eluted from the column by passing an eluent through the column. The eluent can be passed through the column by any means described above for the sample. The elution step may be repeated once to several times. In certain embodiments, the eluent is incubated on the column for a period of time to increase the efficiency of cell elution. After the purified cells are eluted from the column, they can be analyzed by any means desired.

In some embodiments, the cells are not eluted from the column. Instead, they can be lysed on column or the column bed material with cells bound can be released from the column and subjected to further analysis such as a polymerase chain reaction.

Non-limiting examples of how the columns can be used include the following.
1) capture and release of cells
2) depletion of cells from a complex cellular mixture and retention of remaining cells
3) capture labeled cells, then release and count
4) Capture cells, lyse cells on column or post column. Collect DNA or RNA by DNA prep or RNA prep, or collect proteins or other cellular components and analyze
5) Purify sperm from a crime scene away from other cells and perform DNA analysis to identify the source of the sperm
6) After cell capture, the column is washed and cells can optionally be reacted with a dye to label the captured cells. The resin may be removed from the column and plated or spread on a surface. The resin beads containing attached cells may be sorted and counted or analyzed by any means.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such preferred embodiments.

EXAMPLES

Example 1

Sperm is Captured, Separated from Cells and DNA Analysis is Performed

In forensics, it is often desired to obtain DNA profiles from old stains, body fluid samples and other possible samples. The primary goal is to preferentially separate sperm from vaginal cells and other materials, a necessity for DNA analysis in rape cases, for example.

DNA aptamers which are short strands of DNA were developed by SomaLogic (Denver, Colo.) to bind sperm heads, and used to both identify and immobilize the sperm heads for purification and later DNA analysis. These aptamers are used in a column bed system of the invention with Biotin and Streptavidin linkers to selectively capture sperm cells. The aptamer sequences bind preferentially to both the outer protein membrane and the stripped perinuclear calyx of sperm cells in the presence of non-sperm epithelial cells.

Sperm cells (research vials, prepared by density gradient centrifugation and subsequent washing) are purchased from California Cryobank. Washed sperm cells are prepared using three washes and suspension in a buffer supplemented with Triton X100 detergent and NaCl to final concentrations of 1% v/v and 600 mM. HeLa cells to simulate non-sperm epithelial cells are added and the mixtures are incubated for ten minutes.

Cotton swabs are used to simulate capturing the sperm sample. The sample is removed from the cotton swab with a buffer. Aptamers with biotin linkers are added to the solution and incubated. After washing of the sample the mixture is passed through a streptavidin packed bed column of the invention. The sperm is captured and subsequently washed by passing wash buffer through the column.

The sperm is eluted from the column by passing a buffer through the column breaking up the aptamer/sperm column. Eluted aptamer DNA are purified and then amplified for DNA analysis.

Example 2

Antibody Purification of Sperm

This example uses antibodies rather than aptamers to capture sperm cells in the presence of other cells. A cocktail of antibodies specific to sperm cell surface antigens are anchored to Protein A affinity beads packed into a column of the invention. The specificity of antibody-antigen binding selectively captures sperm cells from samples that are comprised of a mixture of sperm cells, white blood cells, epithelial cells, cell lysates, etc. Alternatively, the antibodies are added to the sample mixture first and then captured by the column. After washing with a neutral buffer, the sperm cells are eluted with low pH or high pH buffers and the DNA is analyzed.

The antibodies may be tagged with His tags for example. In this case, IMAC beads may be packed into columns of the invention to capture the antibodies which are used in turn, to capture the sperm. In this case, the antibody sperm combination may be eluted, the cell lysed and the DNA analyzed. Other tags may be used such as FLAG-ANTIFLAG, etc.

Peptide tags are used for capture. These include AviTag, a peptide allowing biotinylation by the enzyme BirA so the protein can be isolated by streptavidin, Calmodulin-tag, a peptide bound by the protein calmodulin, FLAG-tag, a peptide recognized by an antibody, HA-tag, a peptide recognized by an antibody, Myc-tag, a short peptide recognized by an antibody, SBP-tag, a peptide which binds to streptavidin, Softag 1, for mammalian expression, Softag 3, for prokaryotic expression, V5 tag, a peptide recognized by an antibody, and Xpress tag.

Covalent tags include Isopeptag which binds covalently to pilin-C protein and SpyTag which binds covalently to SpyCatcher protein.

Protein tags include BCCP (Biotin Carboxyl Carrier Protein), a protein domain recognized by streptavidin, glutathione-S-transferase-tag, a protein which binds to immobilized glutathione, green fluorescent protein-tag, a protein which is spontaneously fluorescent and can be bound by nanobodies, maltose binding protein-tag, a protein which binds to amylose agarose, Nus-tag, Strep-tag, a peptide which binds to streptavidin or the modified streptavidin called Strep-Tactin and Thioredoxin-tag.

Example 3

Circulating Tumor Cells

A cancerous tumor sheds small numbers of tumorous cells into its immediate vasculature. These cells then make their way into the circulatory system, and are thus called circulating tumor cells (CTCs). CTC information is used cancer prognosis, therapy monitoring and metastasis research.

Circulating tumor cells (CTCs) are important targets for study to understand, diagnose, and treat cancers. However, CTCs are found in blood at extremely low concentrations which makes isolation, enrichment and characterization challenging. A typical concentration in a human cancer patient is approximately 1-100 CTCs per mL of blood.

CTC purification with the columns of the invention capture many or most of the CTCs in the blood sample (high capture efficiency) and are selective with very few other cells accidently isolated. The samples are processed with sufficient speed and without battering of the cells so that cells remain viable in many cases.

The columns of the invention operate by coating the column media with an antibody (anti-EpCAM) and then bonding the antibody to the epithelial adhesion molecules (EpCAM) of CTCs. After capture of anti-EpCAM labeled CTCs from a blood sample, CTC identification and enumeration are achieved using immunostaining.

During one experiment 2 to 80 spiked breast cancer cells are isolated from 1 mL of mice blood sample with 90% capture efficiency. A 200 µL bed column with a 1 mL pipette tip body is used for one experiment. While blood is processed through the column with bidirectional flow for 5 cycles at 200 uL/min flow rate. The column is washed with buffer and then the cells are eluted with 500 mM citric acid.

Example 4

Capture of Cells from Blood

The purification and analysis processes used in example 3 are used for other cells from blood including white blood cells, stem cells, T cells, B cells and other cells.

Example 5

Capture of Cells from Blood

The purification and analysis processes used in examples 3 and 4 are used except the pumping methods for flowing the fluids through the column are changed as follows.
The pumping method is bidirectional, unidirectional, gravity flow and gravity flow plus vacuum and/or pressure.
In addition, the method is performed with two different column configurations. In one configuration, there is an air gap above the column bed, while in the other configuration, there is no air gap above the column bed.

Example 6

Capture of Cells from Blood

The purification and analysis processes used in examples 3, 4 and 5 are used except the column has a bed volume of 1 mL inside a 10 mL pipette body. The flow rates are approximately 10 times faster with this column so samples sizes approximately 10 times greater are processed in approximately the same time.
In this example the cells are released from the column by enzymatic and chemical cleavage of the linker. The cells are collected and counted.

Examples 7

Capture of Cells from Tissue

For tissue samples composed of different types of cells, heterogeneous cell populations will be present. To obtain as much information as possible about an individual cell type, biologists have developed ways of dissociating cells from tissues and separating the various types. A mild procedure is used to collect whole, intact cells. Homogenized cells are kept at low temperatures to prevent autolysis and kept in an isotonic solution to prevent osmotic damage.
The first step in isolating cells of a uniform type from a tissue that contains a mixture of cell types is to disrupt the extracellular matrix that holds the cells together. For example, viable dissociated cells are obtained from fetal or neonatal tissues. The tissue sample is treated with proteolytic enzymes (such as trypsin and collagenase) to digest proteins in the extracellular matrix and with agents (such as ethylenediaminetetraacetic acid, or EDTA) that bind, or chelate, the $Ca^{2+}$ on which cell-cell adhesion depends. The tissue can then be teased apart into single living cells by gentle agitation to make a cell suspension.
Columns of the inventions are loaded with antibodies that have an affinity for fetal cells. The suspension is passed with bidirectional flow through the column to capture the cells. After washing, the cells are released with by treatment with trypsin to digest the antibodies. The cells may be visually tagged by using an antibody coupled to a fluorescent dye to label specific cells.

Given appropriate surroundings, most plant and animal cells can live, multiply, and even express differentiated properties in a tissue-culture dish. The cells can be watched continuously under the microscope or analyzed biochemically, and the effects of adding or removing specific molecules, such as hormones or growth factors, can be explored. In addition, by mixing two cell types, the interactions between one cell type and another can be studied. Experiments performed on cultured cells are sometimes said to be carried out in vitro (literally, "in glass") to contrast them with experiments using intact organisms, which are said to be carried out in vivo (literally, "in the living organism"). These terms can be confusing, however, because they are often used in a very different sense by biochemists. In the biochemistry lab, in vitro refers to reactions carried out in a test tube in the absence of living cells, whereas in vivo refers to any reaction taking place inside a living cell (even cells that are growing in culture).

Example 8

Capture of Bacterial Cells

An *E. coli* culture is grown at 37° C. The *E. coli* strain is engineered using recombinant DNA techniques so that surface proteins on the cell contain histidine tags. A spike of *Salmonella* is added to the sample so that the sample contains 10% *Salmonella* cells, 90% *E. coli* cells, media and other materials.
A 1 mL bed size column containing Ni form IMAC affinity media is used to treat or process a 3 mL sample with unidirectional single pass flow under gravity. Some air pressure is used to push the last remaining solution through the column. The *E. coli* cells are removed from the mixture and are captured on the column while the *Salmonella* cells remain in the sample.

Example 9

Capture of Cells from Culture

Most plant and animal cells can live, multiply, and even express differentiated properties in a tissue-culture dish. The cells can be watched continuously under the microscope or analyzed biochemically, and the effects of adding or removing specific molecules, such as hormones or growth factors can be explored. In addition, by mixing two cell types, the interactions between one cell type and another can be studied. After growing the cells, the specific cells are captured according to processes similar to those described in examples 7 and 8.
After capture, the column is washed and optionally reacted with a dye to label the captured cells. The resin may be removed from the column and plated or spread on a surface. The resin beads containing attached cells may be sorted and counted or analyzed by any means.

Example 10

Companion Diagnostic to Antibody or FAB Based Drug

Often it is unknown whether a particular antibody or FAB drug will be effective against a particular cancer case. The treatment process can be trial and error, trying one drug and then if it is not effective, trying the next drug and so on. Columns of the invention may be used to determine the potential effectiveness of a series of drugs. Tagged drug antibodies and FABs are prepared. A series of columns of the invention are prepared each with a single antibody bound through the tag to the media of the column. In this way, each available drug is represented by a column. Then a blood sample from a cancer patient is treated by the series of columns in an attempt to capture circulating tumor cells. The columns are washed and the cells, if present, are recovered and analyzed by fluorescence, DNA, microscopy or any suitable analytical technology. Specific drugs that may be effective against the cancer are captured containing drug based affinity media. Then a treatment program is designed using the antibody/FAB drugs that have the highest affinity for the tumor.

What is claimed is:

1. A method for purifying viable cells, comprised of:
   a) providing at least one column, wherein the column is comprised of a packed bed of medium, wherein the packed bed of medium has a bed volume, wherein the packed bed of medium is retained between two frits, a lower frit and an upper frit, wherein the packed bed of medium is comprised of particles, wherein the particles are comprised of an affinity group, wherein the affinity group is an antibody or a FAB;
   b) providing a biological sample, wherein the sample is comprised of viable cells, wherein the viable cells are not labeled with antibodies, wherein the biological sample has a sample volume, wherein the sample volume is larger than the bed volume;
   c) aspirating the biological sample in an upward direction through the column, wherein the sample is aspirated through the lower frit, into the packed bed of medium and then through the upper frit;
   d) expelling the biological sample by reversing the flow direction, wherein the biological sample is expelled in a downward direction through the upper frit, into the packed bed of medium and then through the lower frit;
   e) repeating steps (c) and (d) multiple times, wherein the biological sample is not incubated on the column, whereby a portion of the viable cells are captured by the antibody affinity groups on the particles in the packed bed of medium;
   f) passing a wash solution through the column; and
   g) eluting the cells by passing an eluent through the column, wherein the eluted cells are intact and viable, wherein the eluted cells maintain their integrity, wherein the method is at least partially performed by a timed computer-controlled program, and wherein the entire method is performed in less than 30 minutes.

2. The method of claim 1, wherein the column is a pipette tip.

3. The method of claim 1, wherein the sample is comprised of bacterial cells or plant cells.

4. The method of claim 1, wherein following step (f) the captured cells are labeled on the column.

5. The method of claim 1, wherein the antibodies are covalently attached to the particles with a linker.

6. The method of claim 1, wherein the antibodies are tagged with a drug.

7. The method of claim 1, wherein the particles are comprised of protein A or protein G.

8. The method of claim 1, wherein the method is used for negative selection and viable cells captured by the antibody affinity groups are not the cells of interest.

9. The method of claim 1, wherein the eluted cells are selected from the group consisting of tumor cells, circulating tumor cells, immune cells, sperm cells, white blood cells, cancer cells, *E. coli* cells, T cells, B cells and stem cells.

* * * * *